(12) United States Patent
Azzolini

(10) Patent No.: US 6,575,955 B2
(45) Date of Patent: Jun. 10, 2003

(54) HIGH-STERILITY AND HIGH-CAPACITY CONNECTOR FOR LINES FOR OUTFLOW FROM BOTTLES

(76) Inventor: Graziano Azzolini, Via S. Anna, 3/R, 41032 Cavezzo (IT)

( * ) Notice: Subject to any disclaimer, the term of this patent is extended or adjusted under 35 U.S.C. 154(b) by 0 days.

(21) Appl. No.: 09/877,560

(22) Filed: Jun. 8, 2001

(65) Prior Publication Data

US 2002/0188274 A1 Dec. 12, 2002

(51) Int. Cl.[7] .............................................. A61B 19/00
(52) U.S. Cl. ...................... 604/411; 604/403; 604/410; 604/412; 604/413; 604/414
(58) Field of Search ................. 604/403, 410, 604/411, 412, 413, 414

(56) References Cited

U.S. PATENT DOCUMENTS

| | | | |
|---|---|---|---|
| 4,201,208 A | 5/1980 | Cambio, Jr. | |
| 4,675,020 A | 6/1987 | McPhee | |
| 5,279,576 A | 1/1994 | Loo et al. | |
| 5,456,678 A | * 10/1995 | Nicoletti | 600/577 |
| 6,062,230 A | * 5/2000 | Kajgana | 132/115 |

FOREIGN PATENT DOCUMENTS

| | | |
|---|---|---|
| FR | 2 780 878 A1 | 1/2000 |
| GB | 2 171 678 A | 9/1986 |

* cited by examiner

Primary Examiner—William C. Doerrler
Assistant Examiner—Filip Zec
(74) Attorney, Agent, or Firm—Wolf, Greenfield & Sacks, P.C.

(57) ABSTRACT

A high-sterility and high-capacity connector for lines for outflow from bottles for containing fluid-liquid substances for medical use, comprising an elongated cylindrical body, in a lower portion of which an anatomically shaped grip portion is provided and at an upper end of which a protruding piercing element which is functionally combined with means for engaging the rim of the neck of the bottle is provided.

7 Claims, 3 Drawing Sheets

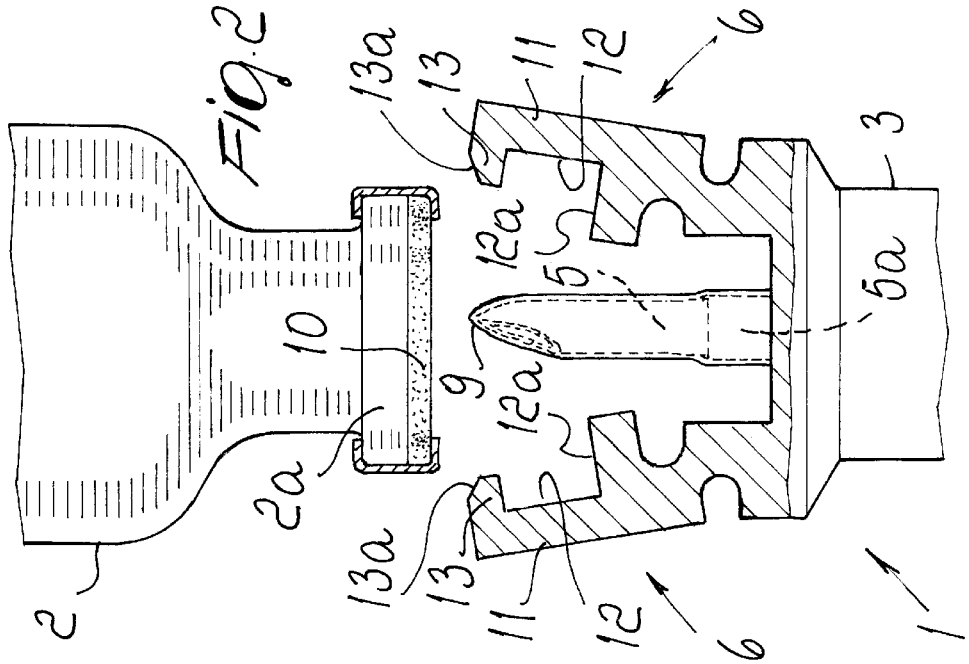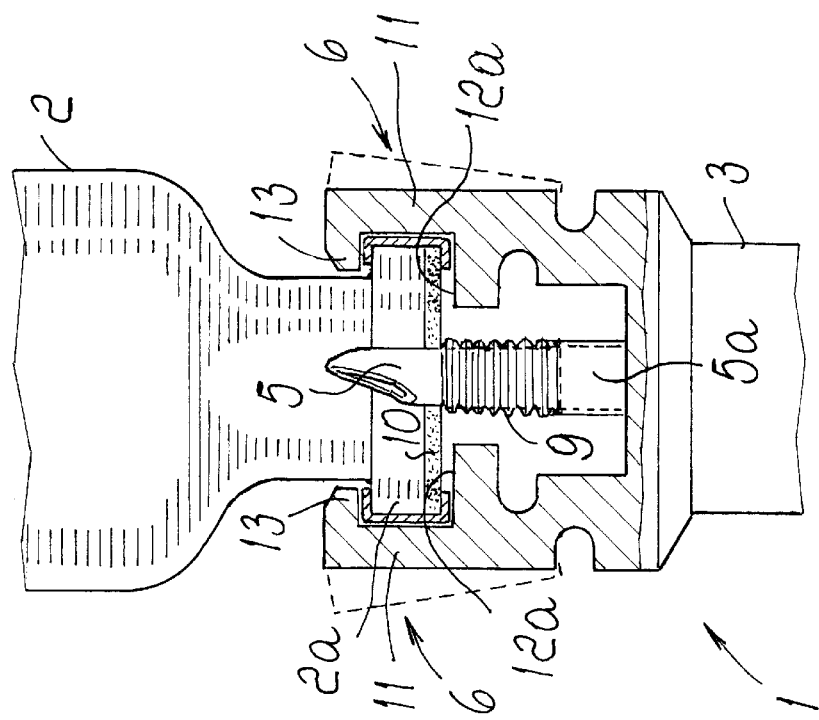

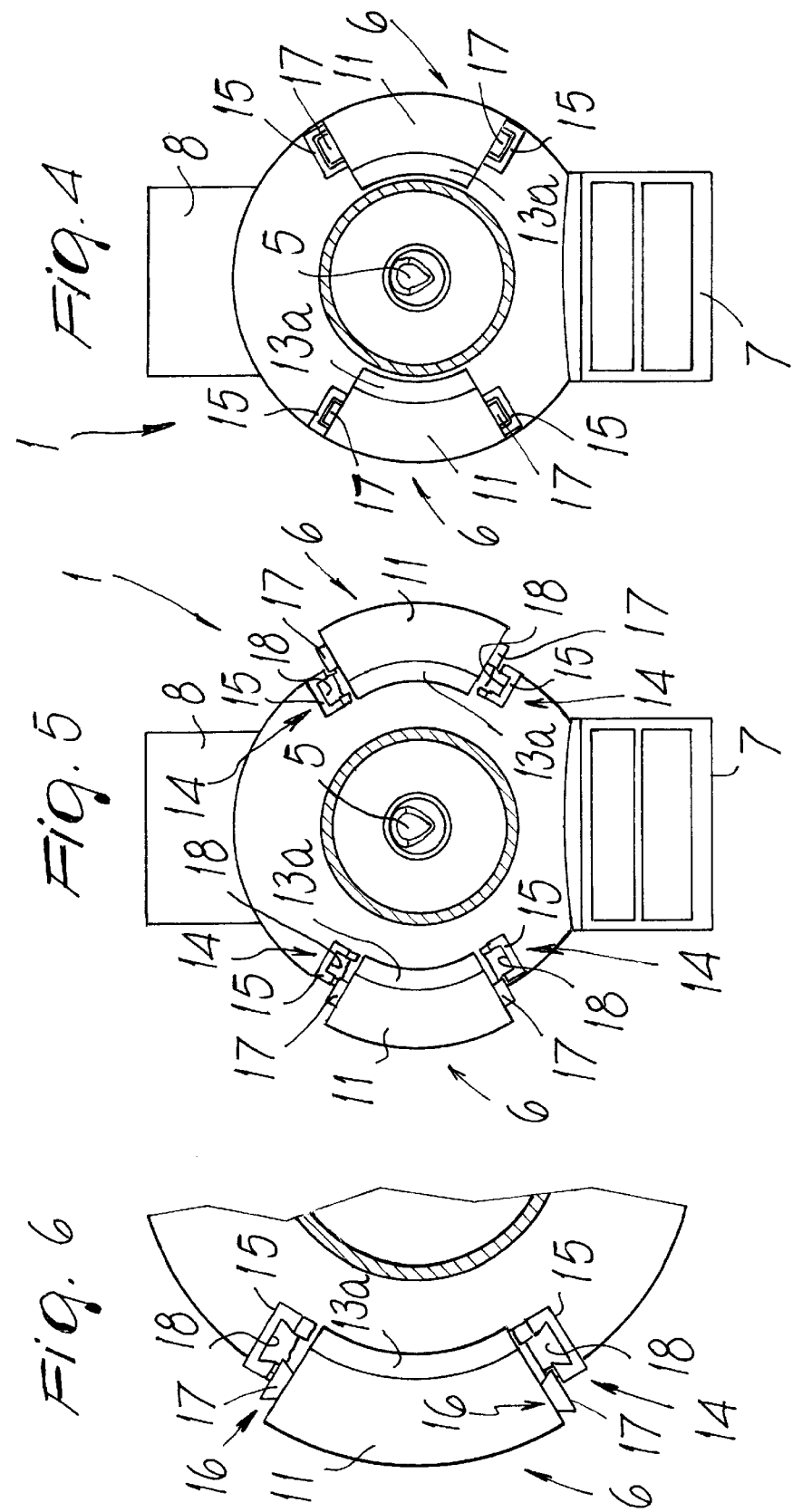

HIGH-STERILITY AND HIGH-CAPACITY CONNECTOR FOR LINES FOR OUTFLOW FROM BOTTLES

BACKGROUND OF THE INVENTION

The present invention relates to a high-sterility and high-capacity connector for lines for outflow from bottles containing fluid-liquid substances for medical use.

Connectors for outflow lines, used to extract liquid or solid drugs to be administered to patients from their containment bottles, have long been known in the medical field.

These conventional connectors substantially consist of an elongated prism-shaped body having, at its end, a hollow tip or piercing element by means of which, after being pushed firmly by an operator, it penetrates the closure of the bottles, which is conveniently made of elastic material in order to ensure a hydraulic and sterile seal, and directly connects the drug to the outflow line, being equipped with all the administration adjustment devices, such as flow control elements, fastening clamps, filters, additional access ports, et cetera.

One of the most widely occurring problems relates to maintaining the sterility of the entire administration line, which is made of single-use material. This sterility is attacked from outside and endangered by the maneuvers required to provide the connection: the bottle and its closure are preserved in the atmosphere, and the piercing element, after tearing the sterile packaging that protects the connector, is necessarily placed in contact with it and thus becomes a vehicle for conveying bacteria of all kinds, which reach the drug stored inside and, ultimately, the patient.

A second drawback is the limited capacity that conventional connectors allow to achieve.

The passage section for the outflowing drug is in fact substantially limited, and therefore operators, if necessary, resort to fully removing the closure of the bottles in order to be able to have, when required, a significantly higher capacity, particularly in the case of viscous liquids such as e.g. contrast liquids for imaging-based diagnostics.

This entails removing from the bottle, with troublesome maneuvers and possibly by using makeshift tools which as such are dangerous for the safety of the operators who risk injuring themselves, first the metal collar that holds the closure in place and then the closure itself, leaving the mouth of the bottle fully unprotected from contamination.

A third drawback is the intentional or accidental possibility of reusing a same connector more than once and for a plurality of drugs, violating the specific strictly single-use characteristics for which such connectors are manufactured and marketed, since in conventional connectors there is no provision to avoid this possibility.

SUMMARY OF THE INVENTION

The aim of the present invention is to solve the above-noted drawbacks of the prior art by providing a high-sterility and high-capacity connector for lines for outflow from bottles for containing fluid-liquid substances for medical use which allows to keep the field of action of the entire outflow line as sterile as possible, despite the maneuvers required in order to provide connection to the bottles, allows to increase satisfactorily the capacity if required, and finally is absolutely not reusable after its first use.

This aim and other objects, which will become better apparent hereinafter, are achieved by a high-sterility and high-capacity connector for lines for outflow from bottles for containing fluid-liquid substances for medical use, characterized in that it comprises an elongated cylindrical body having, in a lower portion thereof an anatomically shaped grip portion and at an upper end thereof a protruding piercing element being functionally combined with means for engaging a rim of the neck of the bottle.

BRIEF DESCRIPTION OF THE DRAWINGS

Further characteristics and advantages of the invention will become better apparent from the description of a preferred embodiment of a high-sterility and high-capacity connector for lines for outflow from bottles for containing fluid-liquid substances for medical use, illustrated only by way of non-limitative example in the accompanying drawings, wherein:

FIGS. 2 and 3 are sectional views of the upper region of the connector and of the neck of a bottle, respectively in the configurations for preparation for coupling and after coupling has been completed;

FIGS. 4 and 5 are top views of the upper end of the connector according to the invention, shown respectively in the configuration for inserting the neck of a bottle, which is not shown for the sake of simplicity, and in the inactive configuration;

FIG. 6 is an enlarged-scale view of a detail of FIG. 5.

DESCRIPTION OF THE PREFERRED EMBODIMENTS

Figure 1:
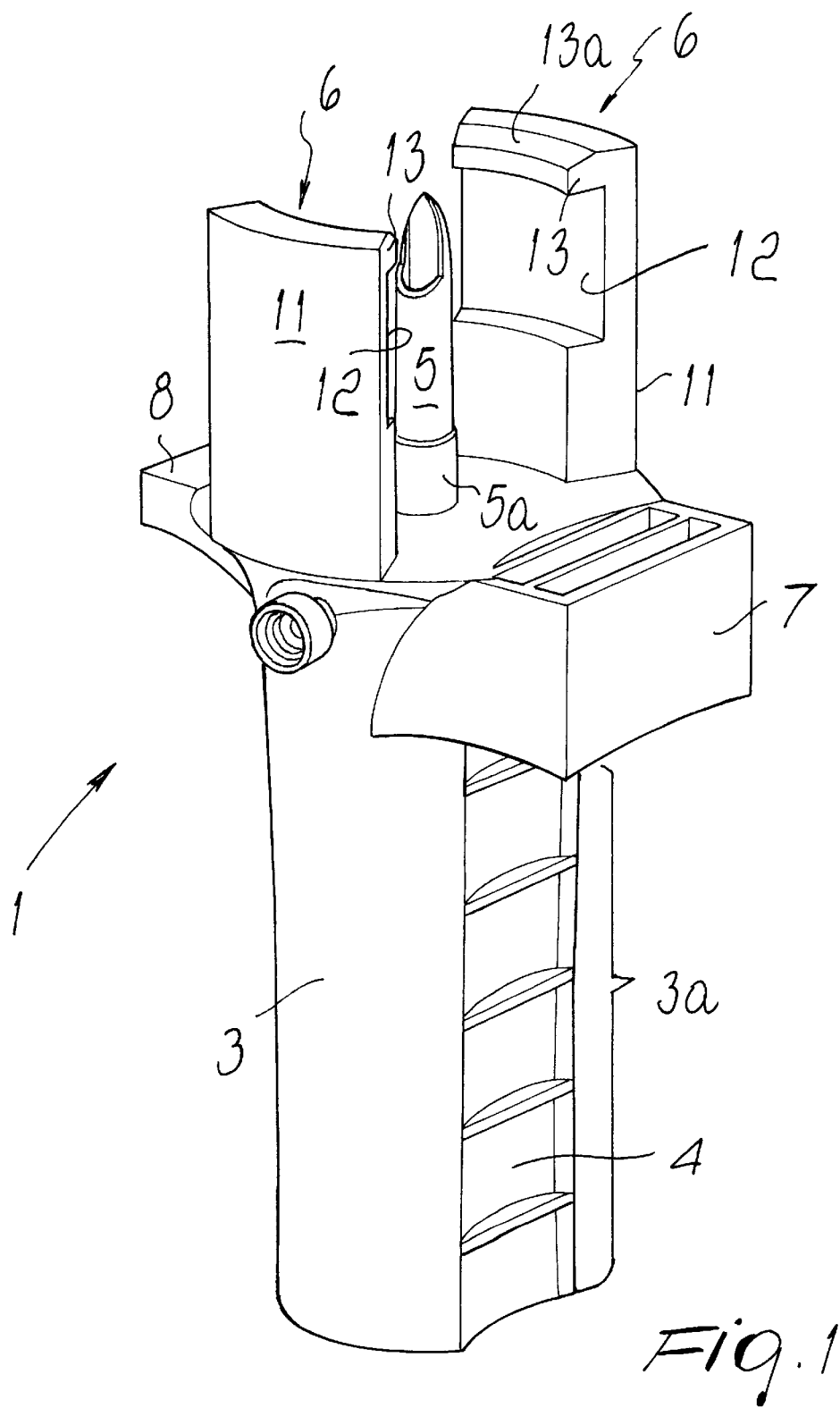
FIG. 1 is a perspective view of the connector according to the invention.

With reference to the figures, the reference numeral 1 designates a high-sterility and high-capacity connector for lines for outflow from bottles 2 which contain substances in the fluid or liquid state for medical use.

The connector 1 comprises a cylindrical elongated body 3, in a lower part 3a of which an anatomically shaped grip portion 4 is provided, while a piercing element 5 functionally combined with means 6 for engaging a rim 2a of the neck of the bottle 2 protrude at the upper end.

The grip portion 4 forms, proximate to its upper part, at least one pair of shoulders 7 and 8 which protrude laterally in opposite directions in order to allow antislip resting and active pushing with one hand by an operator.

The piercing element 5 is completely enclosed by a flexible cap 9 for sterile protection which is rigidly coupled to the base 5a of the piercing element and is adapted to automatically break at the tip and gather on the base 5a as the piercing element is gradually inserted in the closure 10 of the bottle 2.

The means 6 for engaging the rim 2a of the neck of the bottle 2 are constituted by at least one pair of first elastic posts 11 which are arranged so as to face each other and are diametrically opposite with respect to the piercing element 5 and parallel thereto.

The first posts 11 form, internally and in an upper central region, respective cavities 12 being adapted to snugly receive the rim 2a and, at their respective upper ends, corresponding hook-shaped beaks 13 which are directed towards the center, are adapted to engage the rim 2a and have, on their outer surfaces, inclined guiding regions 13a for the insertion of the rim 2a.

Moreover, the engagement means 6 can be equipped with tamper-resistant means 14 when they are in the configuration in which they are closed on the rim 2a; the tamper-resistant means are constituted by at least two pairs of second elastic posts 15, each of which being arranged so as to protrude bilaterally with respect to each first post 11 and substantially in contact therewith.

Interlocking means 16 of the male-female type are interposed between the mutually contacting faces of the first posts 11 and the second posts 15 and are constituted by prism-shaped teeth 17 which protrude from a pair of such contacting faces, constituted by the faces of the posts 11 in the illustrated example, for interpenetrating and permanent engagement with corresponding female seats 18 which are complementary to the prism-shaped teeth 17 and are formed in the opposite pair of faces of the posts 15.

For safer and more stable coupling, both the teeth 17 and the female seats 18 have a profile which is splayed correspondingly outward for the teeth 17 and inward for the seats 18.

In this configuration, the connector 1 is associable with a conventional outflow line also having aspirator means of the manually or automatically activated type.

The operation of the invention is as follows: the operator grips with his hand the grip portion 4, resting against the shoulders 7 and 8.

With his other hand, he grips a bottle 2 and places the mouth of the bottle in contact with the posts 11.

By pushing more firmly on the connector 1 towards the bottle 2, the posts 11 expand slightly elastically until they allow the passage of the rim 2a of the neck, being facilitated in this maneuver by the inclined guiding regions 13a.

As the pushing action continues, the piercing element 5 begins penetration in the closure 10 of the bottle 2 after tearing its own protective cap 9 which, as the piercing element 5 gradually penetrates the closure, gathers just as gradually at the base 5a of said piercing element.

This gradual sliding exposes the piercing element 5 as it advances inside the bottle 2, thus avoiding contact with the surrounding contaminating atmosphere and any contact by the assigned operators.

When penetration is about to be completed, the rim 2a abuts against the end walls 12a of the cavities 12, forcing the posts 11 to rotate inward and automatically aligning the teeth 17 with the seats 18.

The posts 11 thus close around it and lock it (see FIG. 3) with the hook-shaped beaks 13.

Simultaneously, the posts 15, which are forcibly kept pushed out by the teeth 17 when the teeth are extracted from the seats 18, i.e. when the connector 1 is disconnected from the bottle 2, react elastically, rotating towards the respective posts 11 in order to return to their natural vertical position. The teeth 17 thus enter, with an interlocking action, the cavities 18, preventing any possibility of axial translational motion of the connector 1 with respect to the bottle 2.

For the sake of greater stability of the resulting interlocking, both the teeth 17 and the corresponding seats 18 are slightly splayed so as to make it even more difficult for the teeth to exit from the seats and thus render the coupling between the connector 1 and the bottle 2 irreversible and tamper-resistant.

Any traction applied to the bottle 2 or to the connector 1 so as to attempt to disengage them in fact does not generate force components which are directed radially or in any case outward between the seats 18 and the teeth 17, which accordingly continue to prevent any mutual axial translational motion.

The entire engagement operation occurs without requiring the operator to touch or make contact with the elements adapted to provide the outflow of the drug, which thus substantially maintains the sterility characteristics imparted thereto during preparation.

The connector 1 can be advantageously applied to a conventional outflow line which has, in addition to the usual devices for flow adjustment and blocking, devices for insertion of other drugs and air intakes with sterile protection, a suction pump which can produce suction in the entire line, including the connector 1, which thus delivers the maximum possible capacity without having to remove the closure 10 and the corresponding band that retains it on the neck of the bottle 2.

In practice it has been found that the described invention achieves the intended aim and objects.

The invention thus conceived is susceptible of numerous modifications and variations, all of which are within the scope of the appended claims.

All the details may further be replaced with other technically equivalent ones.

In practice, the materials used, as well as the shapes and the dimensions, may be any according to requirements without thereby abandoning the scope of the protection of the appended claims.

What is claimed is:

1. A high-sterility and high-capacity connector for lines for outflow from bottles for containing fluid-liquid substances for medical use, comprising an elongated cylindrical body having, in a lower portion thereof an anatomically shaped grip portion and at an upper end thereof a protruding piercing element which is functionally combined with means for engaging a rim of the neck of the bottle, wherein said means for engaging said rim of the neck of the bottle are constituted by at least two first elastic posts which are arranged so as to face each other and are diametrically opposite with respect to said piercing element and parallel thereto, said first posts forming internally, in a central upper region, respective cavities for snug reception of said rim of the neck of the bottle and, at respective upper ends thereof, corresponding hook-shaped beaks which are directed towards the center and are adapted to engage said rim of the neck, means being provided for preventing any tampering with said engagement means in a configuration in which they are closed on said rim of the neck, and wherein said tamper-resistant means are constituted by at least two pairs of second elastic posts which are each arranged so as to protrude bilaterally with respect to each first post and substantially in contact therewith, interlocking means of the male-female type being interposed between mutually contacting faces of said first and second posts.

2. The connector according to claim 1, wherein said grip portion forms, proximate to an upper part thereof, at least one pair of shoulders which protrude laterally in mutually opposite directions for antislip resting and pushing with an operator's hand.

3. The connector according to claim 1, wherein said piercing element is fully covered with a flexible cap for sterile protection which is rigidly coupled to a base of said piercing element and is automatically breakable at a tip thereof and can gather at said base of the piercing element as the piercing element is gradually inserted in a closure of the bottle.

4. The connector according to claim 1, wherein said hook-shaped beaks have, on upper regions thereof, flared regions for guiding insertion of said rim of the neck of the bottle.

5. The connector according to claim 1, wherein said interlocking means are of male-female type and constituted by prism-shaped teeth which protrude from a pair of said faces for permanent interpenetrating engagement with corresponding female seats which are shaped complementarily to said prism-shaped teeth and are formed in the opposite pair of said faces.

6. The connector according to claim 5, wherein said teeth and said female seats have a profile which is splayed correspondingly towards the outside and the inside of said faces in order to maintain the stability of the interlocking configuration.

7. The connector according to claim 1, wherein said connector is associable with a conventional outflow line which can be provided with manually or automatically activated aspirator means.

* * * * *